US006402776B1

(12) United States Patent
Martin

(10) Patent No.: US 6,402,776 B1
(45) Date of Patent: Jun. 11, 2002

(54) APPARATUS INDUCING PHYSICAL AND MENTAL RELAXATION, BY FLOW OF A TEMPERED LIQUID ON THE FOREHEAD

(76) Inventor: Bertrand Martin, Ruerettes 8, 1800 Vevey (CH)

( * ) Notice: Subject to any disclaimer, the term of this patent is extended or adjusted under 35 U.S.C. 154(b) by 0 days.

(21) Appl. No.: 09/529,436
(22) PCT Filed: Oct. 12, 1998
(86) PCT No.: PCT/CH98/00436
§ 371 (c)(1),
(2), (4) Date: Jan. 22, 2001
(87) PCT Pub. No.: WO99/20220
PCT Pub. Date: Apr. 29, 1999

(30) Foreign Application Priority Data

Oct. 20, 1997 (CH) .................................................. 2435/97

(51) Int. Cl.⁷ ................................................... A61F 7/00
(52) U.S. Cl. ............................... 607/104; 4/516; 4/616; 4/625
(58) Field of Search ................................ 607/104, 109, 607/81–87; 119/73; 4/451.4, 598, 603, 599, 515–523, 602, 621, 625, 626

(56) References Cited

U.S. PATENT DOCUMENTS

| | | | |
|---|---|---|---|
| 2,682,058 A | * 6/1954 | Wolfe | 4/516 |
| 2,850,742 A | * 9/1958 | Glintz | 312/209 |
| 3,088,459 A | * 5/1963 | Rabinoff | 128/206.24 |
| 3,752,399 A | * 8/1973 | Neale et al. | 137/624.14 |
| 4,453,280 A | * 6/1984 | Greenleaf | 4/599 |
| 4,660,233 A | * 4/1987 | Beaver | 4/516 |
| 4,828,709 A | * 5/1989 | Houser et al. | 210/669 |
| 4,834,121 A | * 5/1989 | Bell | 132/272 |
| 4,893,364 A | * 1/1990 | Keller | 4/596 |
| 5,293,654 A | * 3/1994 | Castwell et al. | 4/598 |
| 5,459,887 A | * 10/1995 | Roman et al. | 4/541.4 |
| 5,528,776 A | * 6/1996 | Carmichael | 4/516 |
| 5,784,727 A | * 7/1998 | Perez Garcia | 4/516 |
| 5,813,363 A | * 9/1998 | Snelling | 119/73 |

\* cited by examiner

Primary Examiner—Roy D. Gibson
(74) Attorney, Agent, or Firm—Liniak, Berenato, Longarce & White

(57) ABSTRACT

The invention concerns an apparatus for inducing deep physical and mental relaxation, consisting of a housing containing both a collector (4) and a reservoir (5) wherein are housed a pump (1) and a thermostat heater (2). The liquid contained in the reservoir can be maintained at constant temperature and pumped by a tube (6) to flow onto the patient's forehead whose head rests on the collector. The invention also concerns two other embodiments.

3 Claims, 3 Drawing Sheets

APPARATUS INDUCING PHYSICAL AND MENTAL RELAXATION, BY FLOW OF A TEMPERED LIQUID ON THE FOREHEAD

The present invention relates to an apparatus which allows a warmed liquid, in particular water, to be poured onto the forehead of a supine person, thus inducing a state of deep physical and mental relaxation.

This technique, known as Shirodhara in Indian ayurvedic medicine has, until now, been practised by pouring oil from a pierced pot suspended above the head of the patient. This pot must be frequently refilled. It is difficult to ensure that the oil remains at a constant temperature. In addition to its cost, the oil also has the disadvantage that it runs everywhere (over the head, hair, table, equipment, etc.), making it difficult to maintain hygiene. This technique requires a practitioner present at all times, in order to refill the pot and sweep the patient's forehead with the jet of oil. These operations are also noisy and may distract the patient. The device already known in the art also requires a special massage table to allow the oil to be recovered.

The aim of the invention is to simplify the technique described above and reduce its cost. These aims are achieved using an apparatus according to the invention as claimed in claim 1.

A clearer understanding of the invention and its advantages and characteristics will be gained from the following description of embodiments which are given by way of an example and the attached drawings in which.

Figure 1:
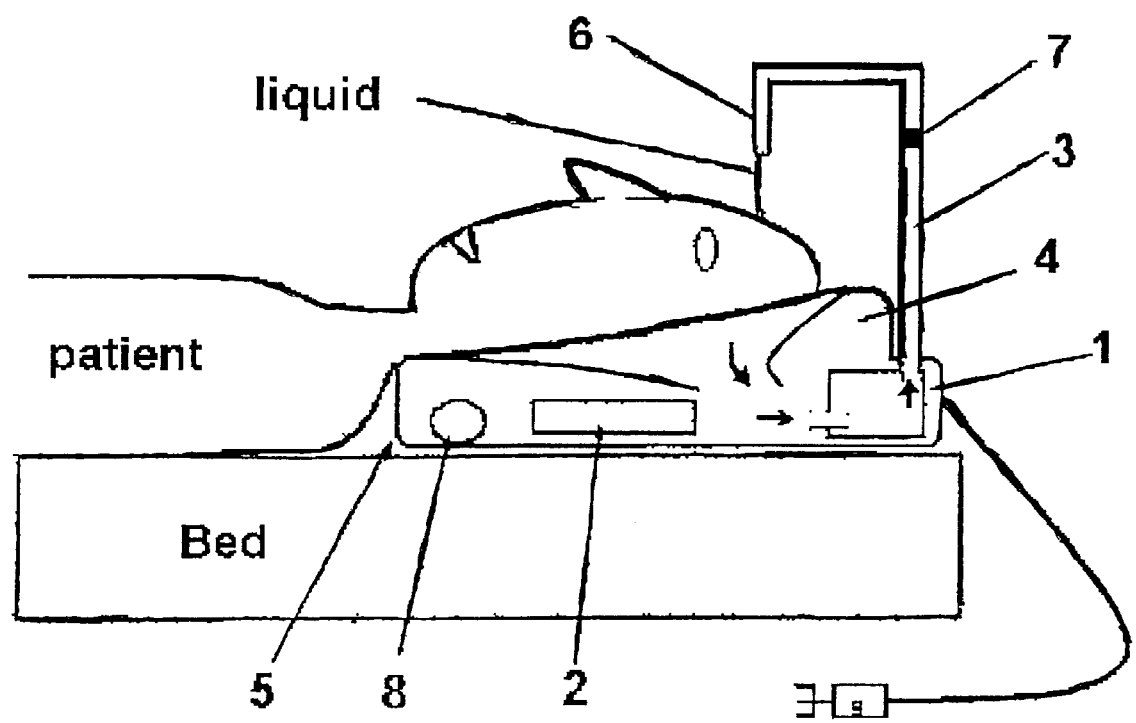
FIG. 1 shows a first example of the apparatus according to the invention.

An apparatus according to the invention uses a pump 1, a thermostatic heating unit 2, a stand 3 and a headrest 4 which acts as a collector in order to recover a liquid, preferably water, stored in a reservoir 5. The liquid which is maintained at a constant temperature by the thermostatic heating unit 2, flows in a closed circuit. From the reservoir 5 the liquid is pumped into a pipe 6 supported by the stand 3 and brought to a point which is at a variable distance from the patient's forehead onto which it flows in a continuous flow, preferably in the centre of the forehead. If required, the apparatus may also comprise a device 7 allowing the flow of liquid to be moved in a continuous lateral movement from side to side in order to sweep across the forehead. The apparatus comprises a timer 8 in order to set the duration of treatment. A safety device may also be provided which will allow the apparatus to be disconnected in case of malfunction.

In the first variant shown in FIG. 1 the apparatus is designed to be portable, therefore all the elements have been arranged in such a way as to form a compact assembly.

Figure 2:
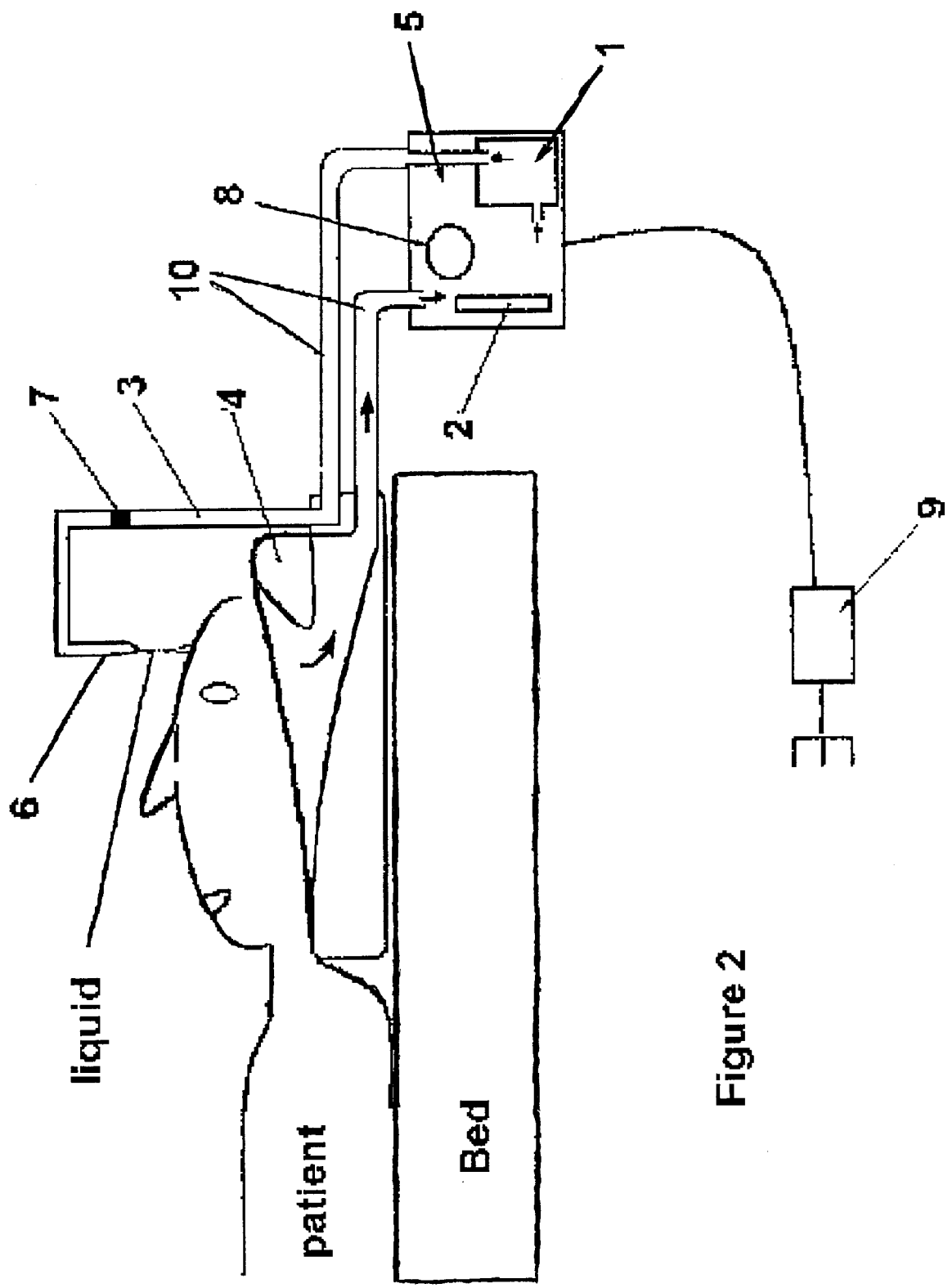
FIG. 2 shows a variant.

FIG. 2 shows a first variant in which the liquid recovery collector is separate from the reservoir containing the thermostat and the pump. The reservoir may be fixed and is connected to the collector by two flexible pipes 10.

Figure 3:
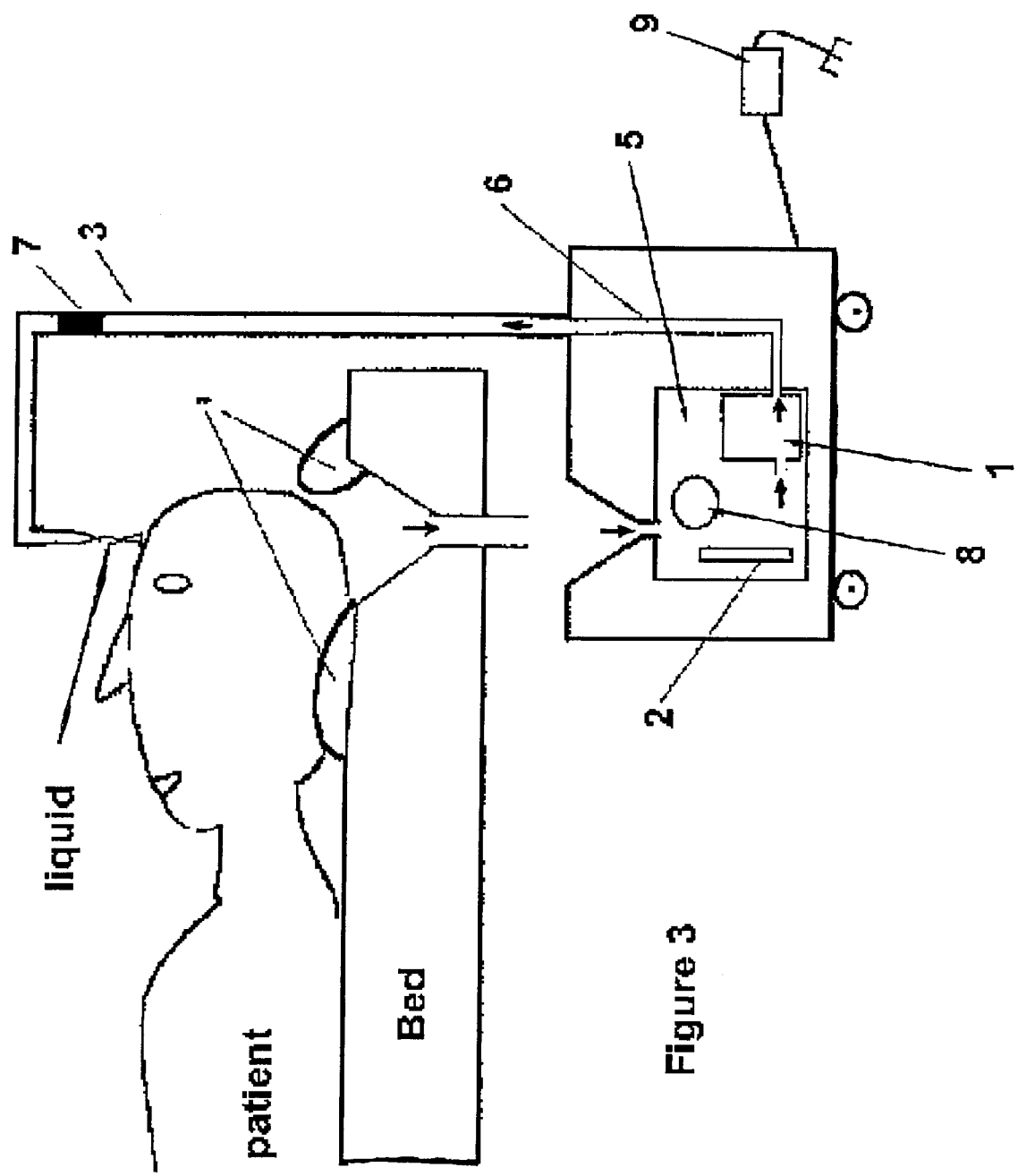
FIG. 3 shows a second variant.

FIG. 3 shows a second variant in which the apparatus is not portable. The collector and the reservoir with pump and heating unit are mounted on a stand on castors allowing the Shirodhara to be carried out on a patient lying on a massage table.

What is claimed is:

1. Apparatus allowing the ayurvedic technique of Shirodhara to be used, consisting in inducing a state of deep relaxation by allowing a liquid to automatically fall onto the forehead in a continuous flow, comprising a headrest for maintaining the forehead in a predetermined supine position, a collector for delivering said liquid to a reservoir, a pump for delivering said liquid from said reservoir to a distribution pipe directing fluid toward the forehead, a thermostatic unit for controlling a temperature of the liquid, a timer and a stand supporting the distribution pipe.

2. Apparatus as claimed in claim 1, further comprising a sweeping device for moving the distribution pipe lateral across an area defined by the forehead.

3. Apparatus as claimed in claim 1, said headrest, said collector, said reservoir, said pump, said distribution pipe, said thermostatic unit, said timer and said stand form a portable device.

* * * * *